(12) United States Patent
Bolkhovets et al.

(10) Patent No.: US 9,078,464 B2
(45) Date of Patent: Jul. 14, 2015

(54) COMPOSITIONS OF PHYTOSTEROLS WITH ENHANCED BIOAVAILABILITY

(75) Inventors: Sergej Bolkhovets, Taby (SE); Atte Kumpulainen, Hasselby (SE)

(73) Assignee: EDIO HEALTHCARE AB, Stockholm (SE)

( * ) Notice: Subject to any disclaimer, the term of this patent is extended or adjusted under 35 U.S.C. 154(b) by 473 days.

(21) Appl. No.: 12/863,451

(22) PCT Filed: Feb. 6, 2009

(86) PCT No.: PCT/SE2009/050127
§ 371 (c)(1),
(2), (4) Date: Jul. 19, 2010

(87) PCT Pub. No.: WO2009/099392
PCT Pub. Date: Aug. 13, 2009

(65) Prior Publication Data
US 2010/0291198 A1 Nov. 18, 2010

(30) Foreign Application Priority Data

Feb. 6, 2008 (SE) .................................... 0800272

(51) Int. Cl.
| | | |
|---|---|---|
| *A23L 1/035* | (2006.01) | |
| *A61K 47/12* | (2006.01) | |
| *A61K 47/14* | (2006.01) | |
| *A61K 9/14* | (2006.01) | |
| *A61K 31/575* | (2006.01) | |
| *A61K 9/16* | (2006.01) | |
| *A61P 3/06* | (2006.01) | |
| *A23L 1/30* | (2006.01) | |
| *A23L 1/00* | (2006.01) | |
| *A61K 9/19* | (2006.01) | |
| *A61K 9/20* | (2006.01) | |

(52) U.S. Cl.
CPC ............. *A23L 1/3004* (2013.01); *A23L 1/0017* (2013.01); *A23L 1/035* (2013.01); *A23L 1/3006* (2013.01); *A23L 1/3008* (2013.01); *A61K 9/145* (2013.01); *A61K 9/19* (2013.01); *A61K 9/2077* (2013.01); *A61K 31/575* (2013.01); *A61K 47/12* (2013.01); *A61K 47/14* (2013.01)

(58) Field of Classification Search
CPC .................................................... A61K 31/575
See application file for complete search history.

(56) References Cited

U.S. PATENT DOCUMENTS

| | | | | |
|---|---|---|---|---|
| 3,865,939 | A | * | 2/1975 | Jandacek ...................... 514/182 |
| 6,110,502 | A | * | 8/2000 | Burruano et al. ............. 424/499 |
| 7,141,265 | B2 | * | 11/2006 | Sakuma et al. ............... 426/601 |
| 2006/0024352 | A1 | | 2/2006 | Poxon et al. |
| 2006/0035871 | A1 | | 2/2006 | Auweter et al. |
| 2006/0234948 | A1 | | 10/2006 | Empie et al. |
| 2006/0251790 | A1 | | 11/2006 | Perlman et al. |
| 2008/0220051 | A1 | | 9/2008 | Horlacher et al. |

FOREIGN PATENT DOCUMENTS

| | | |
|---|---|---|
| DE | 10 2005 039 835 A1 | 3/2007 |
| WO | 99/56729 A1 | 11/1999 |
| WO | 99/60869 A1 | 12/1999 |
| WO | 0132031 A2 | 5/2001 |
| WO | 2009/045520 A2 | 4/2009 |

OTHER PUBLICATIONS

Engel and Knorr, Engineering Life Science, 4: 374-377 (2004).*
"DIMODAN", Emulsifiers and their raw materials, DANISCO, accessed at www.soci.org Feb. 29, 2012.*
International Search Report, dated May 27, 2009, from corresponding PCT application.
Bryan Delaney et al., "Oral absorption of phytosterols and emulsified phytosterols by Sprague-Dawley rats", Journal of Nutritional Biochemistry, 2004, pp. 289-295, vol. 15.

* cited by examiner

Primary Examiner — Kortney L Klinkel
Assistant Examiner — Lisbeth C Robinson
(74) Attorney, Agent, or Firm — Young & Thompson

(57) ABSTRACT

A method for preparing porous microparticles containing phytosterol, by preparing a homogeneous melt of phytosterol and a partially water soluble component, cooling the melt to obtain an amorphous solid material, processing the material into a fine powder, and bringing the powder into contact with an aqueous phase under stirring conditions. A composition suitable for preparing a porous microparticle containing phytosterol. A porous microparticle containing phytosterol. A pharmaceutical or food product useful for lowering the cholesterol level in blood.

16 Claims, 2 Drawing Sheets

COMPOSITIONS OF PHYTOSTEROLS WITH ENHANCED BIOAVAILABILITY

FIELD OF INVENTION

The present invention pertains to compositions and preparations, with particular emphasis on tablets or pills, for consumption of phytosterols with a view to lowering blood cholesterol levels.

BACKGROUND OF THE INVENTION

The origin of cardio-vascular disease in individuals often displays a complex background due to hereditary and age-related issues, but, in addition, also life-style dependent, so-called modifiable risk factors. When added together, these factors can be applied to account for the individual risk of developing cardio-vascular disease [1, 2]. One of these factors is the blood concentration of cholesterol. High serum levels of cholesterol, and in particular high levels of LDL-cholesterol (Low Density Lipoprotein), are epidemiologically strongly linked to an increase in the likelihood of developing of cardiovascular disease [3].

The classification of circulating cholesterol vehicle particles is derived from their settling under centrifugation. Consequently they are referred to as Very Low, Low, Intermediate and High Density Lipoproteins. The High Density Lipoprotein (HDL) is, contrary to the other particles, epidemiologically linked to a decrease in risk for developing cardio-vascular disease.

Chiefly two proteins are associated with the different particles, lipoprotein Al associated with HDL and lipoprotein B, associated with VLDL, LDL and IDL. As the proteins are found in discrete numbers for each of the particles, e.g. one copy of apolipoprotein B is found for each LDL-particle, it appears that determining the apolipoprotein blood concentration effectively yields a measure of the number of particles in circulation. Nowadays it is generally agreed that a treatment target should also include improving the lipoproteins and consequently it is becoming increasingly a routine matter in clinical practice to determine the lipoprotein concentrations as well as the blood cholesterol concentrations [4].

Cholesterol is a vital part of eukaryotic animal cells, with an important function in balancing the fluidity of the cellular membrane. In addition, cholesterol is the starting material for biosynthesis of e.g. vitamin D, cholic acids and various hormones [5]. Plant cells, on the other hand, rely on a whole family of chemically closely related phytosterols for similar functions. The chief difference between phytosterols and cholesterol resides in a substitution (commonly methyl- or ethyl-) on carbon 24 according to the sterol nomenclature [6].

Sterols belong to the category triterpenes. 4000 different triterpenes have yet to date been isolated; roughly 100 of these can be classified as phytosterols [7,8]. Interestingly, plant cells have developed a host of sterols, whereas animal cells have retained only one, cholesterol. The most prevalent of the phytosterols are the so-called 4-desmethyl-sterols, of which sitosterol, stigmasterol, campesterol, brassicasterol and avenosterol are the most prevalent. 4-methyl- and 4,4-dimethyl-sterols are usually less abundant and used as raw material for biosynthesis of 4-desmethyl-sterols [8]. Furthermore, the most commonly found sterols generally carry a double bond at carbon 5, subsequently they are referred to as $\Delta^5$-sterols. Fully saturated sterols, so-called stanols, can also be isolated from cereal sources, in particular rye and wheat. Phytosterols can be extracted from the oily parts of the plant, and hence also from the corresponding vegetable oils, such as corn, canola or tall oil [9].

As phytosterols are found in practically all plant materials typical western diets contain some 100 to 400 mg of phytosterols per day, the diet of vegetarians evidently being placed in the upper part of this interval [10]. In spite of the great chemical similarities between cholesterol and phytosterols a marked difference in the response to consumption of these molecules can be detected. Whereas cholesterol is efficiently absorbed from the intestine, phytosterols, on the other hand, are for all practical purposes hardly absorbed at all. Moreover, there are stark differences in response to the different molecules in the serum. Cholesterol is stored in the body, whereas phytosterols are usually rapidly expelled through the bile. The molecular differences result in the efficient blocking of cholesterol absorption by phytosterols in the intestine.

The cholesterol lowering properties of phytosterols were first documented in the early 50's with studies performed by Peterson on the cholesterol absorption in chickens fed phytosterol enriched fodder [11]. The understanding of the effect of phytosterols on animals and human subjects was improved with the work of Pollak, Best and Farquar and many others [12]. Typically, cholesterol lowering on the order of 10% is reached upon consumption of adequate doses of phytosterols with an almost exclusive decrease in the LDL-cholesterol serum levels; neither the HDL-cholesterol nor the triglyceride serum levels are significantly affected [13].

Cytellin, a cholesterol lowering preparation based on crystalline phytosterols was launched by Eli Lilly as early as 1955. The product had some severe flaws, such as a poor sensory profile and, more importantly, a substantial daily dosage required for clinical efficacy—in the range of tens of grams. Hence, the product was withdrawn from the market in 1982. In 1995, however, Raisio launched Benecol®, a yellow fatty spread based on a patented method for preparing stanols, hydrogenated sterols, esterified with fatty acids. By linking the stanol with fatty acids through esterification an increase in oil solubility by an order of magnitude was obtained. In addition, a considerable increase in stanol/sterol physiological efficacy was observed, where 10 to 15% of LDL-cholesterol reduction could be reached at daily dosages in the range of 1 to 3 grams. Since 1995 a number of similar products and technical solutions have been presented [9].

A number of theories have been presented to account for the cholesterol lowering mechanism of phytosterols, e.g. competition in micelles in the intestine, blocking of cellular receptors on the intestine wall and/or increase in reverse transport back into the intestinal lumen. Irrespective of the exact mechanism, the cholesterol lowering efficacy depends on the reduction of cholesterol absorption into the serum by approximately 50%. Importantly, the phytosterols themselves are poorly absorbed, around 5%, in comparison to around 60% for cholesterol. In addition, the rapid expulsion through the biliary route reduces the circulating phytosterol to less than 1% of the total sterol pool in a healthy individual. Moreover, phytosterols are not converted into cholesterol, or vice versa, in mammals, whereby the circulating phytosterols solely originate from consumed foods. However, neither crystalline phytosterols nor phytosterol esters are in fact directly available for cholesterol lowering purposes, rather the phytosterol molecules have to reside in a hydrolyzed and dissociated form to actively affect the cholesterol absorption process in the intestine [14].

Technical solutions for delivering phytosterol-enriched preparations can be subdivided into two main categories, viz.:

i) chemically, i.e. by covalent bonding, altered phytosterols, e.g. esterified phytosterols or phytostanols; and ii) physico-chemically modified phytosterols, relying on weak physical interactions for maintaining the phytosterol molecules in a bioavailable, physiologically active form.

Due to their low melting point and enhanced oil solubility esterified phytosterols can usually, by emulsification with partially hydrolyzed lipids and cholic acids, form systems exhibiting rather small drop sizes and hence large surface area readily available for lipase activity in the intestine. In turn, the lipase hydrolyzes the covalent bond between the fatty acid and the phytosterol releasing phytosterols in monomolecular physiologically active form.

Common problems encountered with the application of esterified phytosterols are; shortened shelf life, which conveys requirements on cooled storage facilities. Moreover, the chemical process steps severely increase production costs and alter the composition and/or chemical structure from the natural composition and structure found in the original plant source.

Technical solutions relying on physico-chemical modification of the sterols include: i) dissolution of sterols, though only to levels of a few percent, in suitable oils, ii) generation of microcrystalline suspensions to guarantee a large available surface between the sterol crystals and surrounding food matrix, and iii) creation of an oil- or water-based emulsion by application of suitable emulsifying agents with or without addition of crystallization inhibitors.

The physiological efficiency of crystalline phytosterols is still very much doubtful, and these preparations are not likely to provide as efficient cholesterol lowering as e.g. a properly formulated emulsion, or phytostanol or phytosterol esters in a suitable oil-based environment.

Emulsion-based technical solutions tend to generate even more severe shelf-life problems than sterol or stanol esters. Moreover, emulsion-based sterol preparations tend to be inherently thermodynamically unstable, i.e. they are regular emulsions (not microemulsions), and as such rely on addition of suitable stabilizing agents for long term stability.

Food matrixes of choice include dairy products such as milk and yoghurts, juices and juice beverages, fatty spreads or cooking oils and bread. Enrichment of most of the mentioned food products with phytosterols involves dilution of the phytosterols to a relatively low concentration, usually well below 10%, in food products with limited shelf-life.

In summary, development of bioavailable, or physiologically active, preparations of phytosterols all have in common that a large available surface needs to be generated in the intestine in order for efficient molecular transport to the active sites to take place and facilitate lipase and esterase activity.

Due to the relatively large recommended dosage of 1 to 3 grams per day most phytosterol-enriched foods have dosages in the range of 20 to 40 grams of spread, or 100 to 200 ml of beverage. Hence, the prior art technical solutions are inadequate for preparing dry and, with respect to phytosterols, highly concentrated and physiologically highly active final products, such as tablets, or powders, due to long term stability problems, in some instances low physiological activity of the sterol preparation, or the physicochemical nature of the sterol preparation, e.g. the product is in liquid form.

Development of efficient preparations of phytosterols for producing compact and concentrated vehicles, such as tablets or capsules, in similarity to popular vitamin and mineral preparations would generate great benefits for the producer, as well as consumer of the phytosterol product. The phytosterol preparation would have to be efficiently prepared in order to maintain a highly bioavailable form of the phytosterol preparation even after final formulation and tablet manufacturing without loss of activity. Relatively few patents describe compositions and methods of preparation of phytosterol enriched tablets or pills.

US patent application No. 2006/0024352 describes the manufacturing of dietary supplements enriched with phytosterols in the form of tablets, capsules or suspension. The use of micronized or non-micronized powders of sterols in combination with common tablet excipients is mentioned, but no particular preparation of the phytosterols to enhance physiological activity is described.

US patent application No. 2006/0234948 describes phytosterol compositions containing lignans for the production of tablets containing between 50 to 400 mg of phytosterols. Phytosterols as well as other ingredients are only described as finely dispersed.

US patent application No. 2006/0251790 describes phytosterols recrystallized from triglycerides for tablet or pill applications.

International application WO/9956729 describes a composition containing a cholesterol lowering component; food containing such a composition, and a method to prepare the composition. In said method, the cholesterol lowering component is melted or dissolved in an organic phase under elevated temperature, and the obtained melt or solution, before crystallising or associating in other ways, is distributed in a matrix so that the cholesterol lowering component is stabilised mainly in monomolecular or low associated or "cluster" form. The product obtained is a solid, rubberlike or highly viscous mass.

International application WO/9956729 describes a composition comprising a mixture of a phytosterol and a surfactant as specified therein. Also described is the use of the composition as a pharmaceutical or in a food product.

Stanol-lecithin solutions in chloroform have been used for producing microparticles from a blend of phytostanols and lecithin by means of spray drying followed by granulation with polyvinylpyrrolidon and other excipients. Tablets obtained from this particular composition and preparation method display a statistically significant cholesterol lowering efficacy, however, the method presented seems difficult to apply in an industrial scale [15].

Towards this background it is evident that with respect to cholesterol lowering by use of phytosterol there still is a need for a formulation permitting to deliver a required daily dosage of phytosterol having an enhanced bioavailability, either as a pharmaceutical formulation or as a food product. One object of the present invention is to provide such a formulation.

The present invention is based on the finding that there are means of easily and efficiently preparing particles with high concentrations of phytosterols that do display a considerably increased physiological cholesterol lowering efficacy. The process of the invention involves a number of steps and provides a method suitably applying solely edible food-grade or the corresponding pharmaceutically acceptable ingredients.

SUMMARY OF THE INVENTION

According to a first aspect the invention provides a method of preparing porous microparticles containing phytosterol, by
preparing a homogeneous melt of a composition comprising
(i) a phytosterol component, and
(ii) a partially water soluble component selected from at least one of a C10 to C26 fatty acid, monoglyceride of a C10 to C26 fatty acid, metal salt of a C10 to C26 fatty acid, metal salt of monoglyceride of C10 to C26 fatty acid, surfactant and/or polysaccharide;

allowing the melt to solidify to an amorphous solid material;

processing the amorphous solid material into a fine powder; and bringing the powder into contact with an aqueous phase under stirring conditions.

According to another aspect, the invention provides a composition suitable for preparing a porous microparticle containing phytosterol by subjecting it to the method of the invention, comprising
(i) a phytosterol component, and
(ii) a partially water soluble component selected from at least one of a C10 to C26 fatty acid, monoglyceride of a C10 to C26 fatty acid, metal salt of a C10 to C26 fatty acid, metal salt of monoglyceride of C10 to C26 fatty acid, surfactant and/or polysaccharide; for preparing a porous microparticle containing phytosterol.

According to another aspect, the invention provides a solid amorphous material obtained by preparing a homogeneous melt of the inventive composition, and allowing the melt to solidify, said melt being useful for preparing a porous microparticle containing phytosterol.

According to a further aspect, the invention provides a porous microparticle containing phytosterol.

According to a further aspect, the invention provides a granulate obtainable by granulating the inventive porous microparticles According to still another aspect, the invention provides the use of the porous microparticles or granulate of the invention to prepare a pharmaceutical composition for lowering the level of blood cholesterol.

According to still another aspect, the invention provides the use of the porous microparticles or granulate of the invention to prepare a food product enriched with phytosterol.

According to still another aspect, the invention provides a pharmaceutical composition for lowering the level of blood cholesterol prepared by use of the porous microparticles or granulate of the invention.

According to still another aspect, the invention provides a food product containing phytosterol, prepared by use of the porous microparticles or granulate of the invention.

Still further aspects and embodiments will be apparent from the following description and the appended claims.

DETAILED DESCRIPTION OF THE INVENTION

Figure 1:
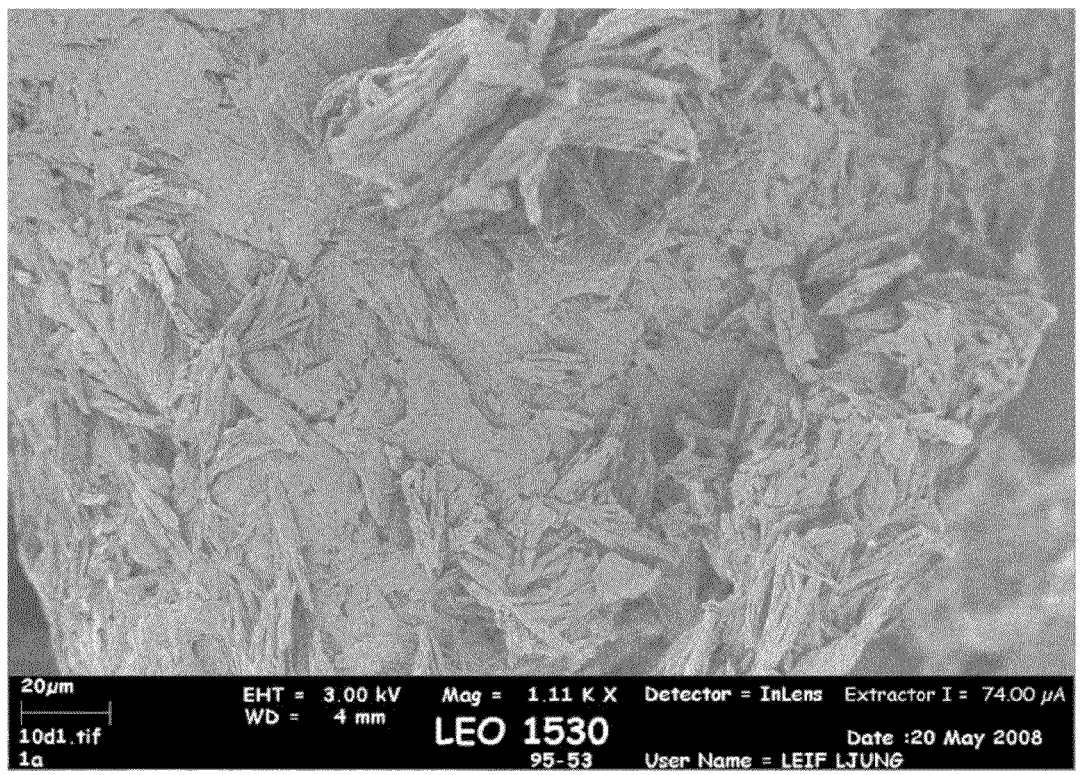
FIG. 1 is a scanning electron microscope (SEM) image of microparticles of the invention, at $1.11*10^3\times$ magnification.

Crystalline sterols have in common that strong van der Waals interactions as well as hydrogen bonding stabilize the crystal structure. In water or aqueous solutions the hydrophobic effect also contributes to effectively minimizing the available area towards the surroundings. This is the main cause behind the comparatively low biological activity of crystalline sterols.

The strong crystalline order can be disrupted by blending with certain agents such as fatty acids or metallic salts of fatty acids, surfactants or monoglycerides. The present inventor has found that an amorphous structure may be generated that very advantageously enables further treatment to obtain a product containing phytosterols having enhanced bioavailability.

Thus, the present inventor has found that an amorphous non-crystalline material can be generated by subjecting a composition comprising a combination of a phytosterol component and a partially water soluble component, as defined herein below, selected from surfactants, fatty acids or derivatives of fatty acids, which amorphous material may be further treated to provide a product containing phytosterols having enhanced bioavailability.

Typically, solubility of hydrophobic or amphiphilic molecules is dependent on temperature, salinity, pH, and, of course, on the presence of other components capable of increasing solubility by e.g. micelle formation. The solubility may be defined as the standard free energy difference of transfer from a dilute aqueous bulk to a neat liquid at 25° C. For example, the solubility of pure stearic acid is about 0.3 mg per liter of water at these particular conditions. On the other hand, addition of e.g. potassium carbonate to an aqueous phase containing stearic acid yields a far greater solubility due to formation of water soluble potassium stearate. Hence, solubility of the partially water soluble component of the invention can be tuned primarily by means of temperature and addition of components to promote solubility.

According to one aspect, the invention provides a composition suitable for preparing a porous microparticle containing phytosterol. Said composition comprises, in addition to the phytosterol component, a partially water soluble component.

The composition according to the invention is processed as described herein below, to generate a molecular blend as a homogeneous mass consisting of only one, amorphous phase.

The phytosterol component primarily comprises sitosterol, sitostanol, campesterol, campestanol and/or stigmasterol, although the exact composition of the phytosterol component depends e.g. on the plant source; also other phytosterols such as brassicasterol, stigmasterol, clionasterol may be present in the phytosterol component. Generally, the phytosterol component will be a mixture of two or more of phytosterols which may be present in the free form or in the naturally occurring ester form. Inexpensive sources of plant sterols are e.g. vegetable oils, vegetable oil sludge, vegetable oil distillates, and other plant oil sources such as tall oils.

The partially water soluble component of the invention is selected from surfactants, fatty acids, derivatives of fatty acids or metal salts of the fatty acids or of the derivatives of fatty acids, or a mixture of any of these.

The fatty acid of the invention suitably is non-branched, saturated or monounsaturated, in particular saturated, and preferably has a carbon chain of between 10 to 26 carbon atoms, or 12 to 24 carbons, e.g. 14 to 22 carbon atoms, or 16 to 20 carbon atoms, e.g. 16 to 18 carbon atoms. For example, it may be selected from lauric (C12:0), myristic (C14:0), palmitic (C16:0), stearic (C18:0), oleic (C18:1), arachidic (C20:0), behenic (C21:0) and erucic (C22:0) acid.

The fatty acid derivative according to the present invention preferably is a mono- or diglyceride of a non-branched, saturated or monounsaturated fatty acid, e.g. a fatty acid as defined herein above. Preferably, it is a monoglyceride or diglyceride of fatty acid selected from fatty acids having a carbon chain of between 10 to 26 carbon atoms, or 12 to 24 carbons, e.g. 12 to 22 carbon atoms, or 12 to 20 carbon atoms, e.g. 12 to 16 carbon atoms, in particular 12 to 14 carbon atoms. For example, it may be a mono- or diglyceride of fatty acid selected from lauric (C12:0), myristic (C14:0), palmitic (C16:0), stearic (C18:0), oleic (C18:1), arachidic (C20:0), behenic (C21:0) and erucic (C22:0) acid. Preferably, the fatty acid derivative is a monoglyceride.

The metal salt of fatty acid or of the derivative of fatty acid suitably is a pharmaceutically acceptable and/or food grade salt, e.g. a salt of a metal such as an alkali metal or an alkaline earth metal, e.g. Li, Na, K, Mg, and Ca, although also other metals such as Zn, Al, Fe, etc. may be used. Preferably, the metal salt is a salt with a monovalent cation, e.g. Na$^+$ and K$^+$, or with a divalent cation, e.g. Mg$^{2+}$ or Ca$^{2+}$. For example, in one suitable embodiment, the metal salt is a salt with a monovalent cation, e.g. Na$^+$.

In one embodiment, the partially water soluble component comprises at least one fatty acid and at least one mono- and/or diglyceride (i.e. monacylglycerol and/or diacylglycerol), or a metal salt of any of these, as defined herein above. For example, the partially water soluble component may comprise at least one fatty acid and at least one monoglyceride and/or a metal salt of any of these.

In case the partially water soluble component comprises both a monoglyceride and a diglyceride the fatty acid component of the mono- and diglyceride preferably is selected from the same group.

The surfactant of the invention suitably is a nonionic, anionic or zwitterionic compound, e.g. a compound having a hydrocarbon chain of between 8 and 20 carbons. The surfactant suitably is pharmaceutically acceptable and/or of food grade quality.

Examples of nonionic surfactants are monoacylglycerols and sucrose esters of fatty acids.

Examples of anionic and zwitterionic surfactants are e.g. lecithin, i.e. compounds within the lecithin group, e.g. fatty substances occurring in animal and plant tissues and in egg yolk, but also from soybean, cotton seed, corn, wheat germ, oat, barley, sunflower, rapeseed, canola, linseed, peanut, palm kernel, generally composed of phosphoric acid, choline, fatty acids, glycerol, glycolipids, triglycerides, and phospholipids (e.g., phosphatidylcholine, phosphatidylethanolamine, and phosphatidylinositol), in particular phosphatidylcholine. Lecithin from any commercially available source is contemplated as useful according to the present invention, e.g. the lecithin may be commercially available egg yolk lecithin or lecithin of vegetabilic origin, e.g. soybean oil lecithin.

The phospholipids that may be used according to the invention may be e.g. phosphatidyl choline, phosphatidyl ethanolamine, N-acylphosphatidyl ethanolamine, phosphatidyl serine, phosphatidyl inositol, phosphatidyl glycerol, diphosphatidyl glycerol, and phosphatidic acid.

Other examples of surfactants include dialkyl sodium sulfosuccinate, polyoxyethylene glycerol, polyoxyethylene stearyl ether, propoxy-ethoxy copolymer, polyoxyethylene fatty alcohol ester, polyoxyethylene sorbitan fatty acid esters, ethoxylated hydrogenated castor oil and butoxylated hydrogenated castor oil, and it should be realized that the exact identity of the surfactant is not material to the invention and that the person of ordinary skill in the art will be able to find many other examples of suitable surfactants for use in the invention.

The composition of the invention suitably comprises from 60 to 95% by weight of phytosterol component, e.g. from 65 to 80% by weight of the phytosterol component, and from 5 to 40% by weight of the partially water soluble component, e.g. from 35% by weight to 20% by weight of the partially water soluble component, e.g. from 30% by weight to 25% by weight of the partially water soluble component.

The weight ratio of the phytosterol component to the partially water soluble component in the composition of the invention preferably is from 1.5:1 to 19:1, more preferably from 1.5:1 to 5:1, e.g. from 2:1 to 4:1 or from 2:1 to 3:1.

In one embodiment, the composition comprises from 1 to 5% by weight of monoglyceride of fatty acid as defined herein above.

In one embodiment, the composition comprises from 5 to 35% by weight of fatty acid as defined herein above.

In one embodiment, the composition comprises from 0.001 to 2% by weight of surfactant as defined herein above.

In one embodiment, the partially water soluble component comprises fatty acid and monoglyceride in a weight ratio that preferably is from 30:1 to 1:1, more preferably from 20:1 to 2:1, e.g. from 15:1 to 5:1, e.g. 14:1 to 6:1.

In one particular embodiment, the composition of the invention comprises a phytosterol component (i) and partially water soluble component (ii) wherein the two components are present in a weight ratio of (i) to (ii) of 60:40 to 80:20, e.g. 65:35 to 75:25, e.g. about 70:30.

In one embodiment, at least one fatty acid is present in the form of a metal salt as defined herein above.

In one embodiment, at least one monoglyceride of fatty acid is present in the form of a metal salt as defined herein above.

In one embodiment, the composition comprises from 0.001 to 0.5% by weight of metal salt of fatty acid and/or of monoglyceride of fatty acid, as defined herein above, in particular of metal salt of fatty acid.

The composition of the present invention, as defined herein above, when treated by the method of the invention, will provide a porous microparticle containing phytosterol of enhanced bioavailability.

Thus, according to one aspect the invention provides a method of preparing porous microparticles containing phytosterol, by preparing a homogeneous melt of a composition comprising a phytosterol component and a partially water soluble component, cooling the melt to obtain an amorphous solid material, processing the material into a fine powder, and bringing the powder into contact with an aqueous phase under stirring conditions.

The homogeneous melt is prepared by heating the composition to a temperature and for a period of time sufficient to melt all components of the inventive composition. Generally, the components are admixed together before heating and heating and melting is performed with stirring so as to obtain a homogeneous melt. However, it should be realized that the components may also be melted separately and mixed together only after melting.

The homogeneous melt is then made to solidify to yield an amorphous solid material, either by rapid cooling, e.g. using liquid nitrogen, or by more slow cooling, suitably under stirring conditions. The formed amorphous solid material may be carried forward directly to the next step or may be stored for later use. Suitably, the material may be stored in a refrigerator, but at any rate should preferably be stored at a temperature under the melting temperature of any of the components of the solid material, e.g. at room temperature.

In the next step of the inventive method, the amorphous solid material is processed into a fine powder. This may be achieved by milling, grinding, grating or any other suitable method of comminuting the material. The particle size of the resultant powder suitably is from 10 to 1000 μm, preferably from 20 to 200 μm. The powder may be carried forward directly to the next step or may be stored for later use.

In the next step of the inventive method, the powder is mixed with an aqueous phase and kept under stirring conditions for a period of time to allow a portion of the partially water soluble component of the powder to dissolve into the water. Said period of time depends primarily on aqueous phase volume, particle size, stirring speed and efficiency, and temperature. However, a period of time typically on the order of 5 to 60 minutes, e.g. 10 to 30 minutes, is required, though it should be realized that also longer times may be used, if deemed appropriate.

Typically, stirring speeds from 100 to 30000 rpm, e.g. 200 to 20000 rpm, or 1000 to 10000 rpm, can be used, depending on exact stirring setup and geometry, temperature of the bulk water phase and concentration and composition of the water soluble added components. The weight ratio of the aqueous phase to powder is typically between 10:1 and 1:10, e.g. from 5:1 to 1:5.

The temperature of the aqueous phase suitably is from 15° C. to 95° C., e.g. from 15° C. to 70° C., e.g. from 20 to 30° C., e.g. about room temperature.

The aqueous phase to be mixed with the powder may be water without any additional component, or an aqueous solution of various substances aiding in the preparation of the porous microparticles of the invention.

For example, the aqueous phase may contain at least one metal salt, e.g. an alkaline or earth alkaline metal salt, e.g. a carbonate, hydrogen carbonate, or hydroxide, such as magnesium, calcium or sodium carbonates or the corresponding hydrogen carbonates or hydroxides. In one embodiment, thus, the aqueous phase contains such metal salt at a concentration of from 0.005 to 2% by weight, e.g. from 0.01 to 1% by weight, of the aqueous phase. These metal salts aid in the dissolution of the partially water soluble component.

Optionally, additional partially water soluble components, such as surfactants, e.g. any of those mentioned herein above, can be present in the aqueous phase to increase treatment efficiency. Suitably, the surfactant, may be present in the aqueous phase at a concentration of from 0.001 to 5%, e.g. from 0.005 to 4%, or from 0.01 to 2%, by weight of the aqueous phase. In one embodiment, the aqueous phase contains lecithin at a concentration of from 0.01 to 2%, by weight of the aqueous phase. The additional partially water soluble components are considered as suspension stabilizing agents.

Furthermore, the aqueous phase may contain component (s) that aid in stabilizing the porous state of the phytosterol microparticles. Such a stabilizing component may be e.g. pectin, starch, modified starch, carrageenan, agar, guar, and gum arabicum, and mixtures thereof. In one embodiment, the aqueous phase comprises 0.005 to 5% by weight, e.g. from 0.01 to 3% by weight of such a stabilizing component.

The porous microparticles can be separated from the aqueous phase by means of filtration, centrifugation, evaporation of water or any known form of separation technique.

The microparticles can be dried, e.g. under vacuum, to yield a product powder with excellent properties with respect to physiological cholesterol lowering activity and sensory performance.

As an example, in one embodiment, the phytosterol component and the partially water soluble component are mixed and melted by heating to yield a homogenous solution. The solution is cooled until solidified and transferred to and milled in a mill. Thereafter, the resulting powder is transferred to an aqueous phase and kept under stirring conditions for a suitable period of time. The phytosterol microparticles then are separated from the aqueous phase by means of filtration and dried under vacuum.

Figure 2:
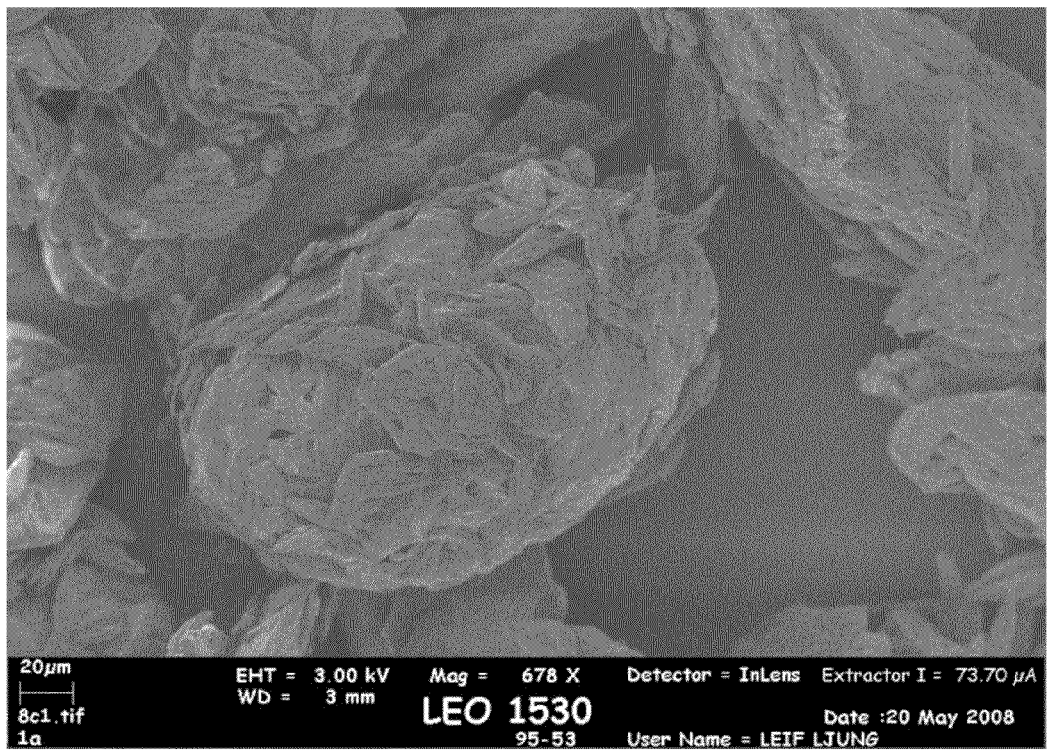
FIG. 2 is a SEM image of microparticles of the invention, at 678× magnification.

Typically a micronized phytosterol preparation of the prior art may exhibit a surface area of approximately 50 $m^2/g$ of phytosterol. It is estimated that by the method of the present invention, microparticles having a surface area of 100 to 500 $m^2/g$ of phytosterol are obtainable. Without wishing to be bound to any theory it is considered that the increase in surface area observed is due in particular to the presence, in the composition, of the partially water soluble component, which aids in lowering surface tension towards the aqueous phase as well as partially dissolves therein, thereby providing a roughened particle surface as well as pores in the microparticles (cf. FIGS. 1 and 2).

During the treatment in aqueous phase, dissolution of partially water soluble component changes the composition of the particles by favoring the retention of less water soluble material in the solid particle phase. The water treatment hence generates a secondary composition, different from the original composition, by the dissolution of components from the particles to the aqueous phase. The compositional change is dependent on equilibrium parameters, such as starting composition, particle size, aqueous phase volume and temperature, as well as on kinetic factors such as stirring speed and efficiency, and treatment time. In addition, due to factors such as filter retention and increased uptake of water to the particles direct gravimetric comparison before and after water treatment rarely yields accurate information on the composition of the secondary composition, i.e. the composition obtained.

The porous microparticle of the invention typically has a particle size of from 10 to 100 µm, e.g. from 10 to 50 µm, such as from 15 to 40 µm, although larger or smaller particles may also be obtained.

The particles may be granulated, by conventional granulation methods as known to the person of ordinary skill in the art, to yield a granulate of a size of e.g. 100 to 1000 µm, e.g. from 100 to 500 µm.

The porous microparticles of the invention can be used in the production of tablets, pills or capsules or added to alimentary products in different ways, either as such or, after granulation, as a granulate.

Examples of alimentary products, into which the porous microparticles may be incorporated, are dairy products (e.g. milk, yoghurt, butter, cheese and spreads), juices and juice drinks, soy or rice based drinks, bread, snacks or confectionery products.

For example, an amount of microparticles corresponding to a daily dosage of 1-3 g phytosterols, e.g. 2 g phytosterols, may be added to 50-200 g of a food product, e.g. 80-150 g of food product, such as 80-150 g of a liquid product.

The microparticles of the invention may be incorporated into an alimentary product by e.g. infusion, injection, mixing, kneading, blending, immersion, spraying, surface application, etc., depending e.g. on the particular alimentary product that is to be enriched with phytosterol.

In connection to the use as an alimentary additive it is noted that, as a further advantageous effect of the method of the present invention, the inventive microparticles are essentially free from any unpleasant taste. Consequently, the microparticles of the present invention, when used as a food additive, will not contribute substantially to the taste or flavor of the food product. Accordingly, the compositions of the present invention can be used in food products without compromising the food products texture, taste and flavor.

Pharmaceutical formulations of the present invention may be e.g. pills, tablets, chewable tablets, coated tablets, soft and hard shell capsules, powders or granulates, e.g. in sachets, etc., including sustained release preparations.

The formulation may be administered to a subject to be treated as a physically discrete unit, in single or multiple dosages, each unit containing a predetermined quantity of phytosterol, optionally in association with a suitable excipient and/or carrier.

The quantity of phytosterol to be administered is such as to produce the desired therapeutic effect upon administration of one or more of pharmaceutical units. The dosage will depend e.g. upon the case history of the subject treated, the age, health, and weight of the subject etc., and suitably is determined by the attending physician. Generally, the daily dosage can range from about 0.5 to about 3 g phytosterol, given in one or several daily doses, e.g. 1-6 daily doses, or 1-3 daily doses. As an example, a daily dosage of 1.5 g phytosterol may be administered in dosage units, e.g. chewable tablets, containing 500 mg phytosterol each.

The concentration of phytosterol in the pharmaceutical formulation may be very high, due to the advantageous properties of the porous microparticle of the invention. For example, the phytosterol may be present at a weight ratio of up to 95% in a pharmaceutical formulation of the invention, or up to 80%, or up to 70%. As an example, a chewable tablet, prepared by use of the porous microparticles of the invention may contain 500 mg of phytosterols for a total tablet weight of 1.4 g, or may contain 700 mg of phytosterols for a total tablet weight of 1 g.

The pharmaceutical formulation of the invention may comprise conventional, pharmaceutically acceptable exipients, such as wetting agents, lubricants, coloring agents, flavoring agents, and preservatives, and/or carriers, as well-known to those who are skilled in the art.

The pharmaceutically acceptable carrier suitably is chemically inert to the other components of the formulation and has no detrimental side effects or toxicity under the conditions of use. Pharmaceutical formulations are found e.g. in Remington: The Science and Practice of Pharmacy. A. R. Gennaro, Editor. Lippincott, Williams and Wilkins, latest edition. Some examples of the substances that can act as carriers are sugars such as xylitol, lactose, glucose, and sucrose; starches such as corn starch and potato starch; cellulose and its derivatives, such as sodium carboxymethyl cellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil as well as other non-toxic compatible substances used in preparation of formulations.

Pharmaceutical capsules can contain the phytosterol microparticles in granulated form granules, which may be mixed with fillers such as lactose, binders such as starches, and/or lubricants such as talc or magnesium stearate and, optionally, stabilizers.

The invention is illustrated by, but not restricted to, the following examples.

EXAMPLES

Example 1

70 g of phytosterols, 26 g of stearic acid and 4 g of monoglyceryl myristate are mixed and melted by heating to yield a homogenous solution at an estimated solidification point of approximately 95° C. The solution is cooled and transferred to and milled in a mill. Thereafter the resulting powder is transferred to 0.5 l of water at room temperature and gently stirred, 100 rpm with a paddle stirrer. After 30 minutes of stirring the phytosterol microparticles are separated from the water solution by means of filtration and dried under vacuum. Yield: 98.7 g of phytosterol microparticles with an average size of 30 μm.

Example 2

70 g of phytosterols, 26 g of stearic acid and 4 g of monoglyceryl myristate are mixed and melted by heating to yield a homogenous solution at an estimated solidification point of approximately 95° C. The solution is cooled and transferred to and milled in a Colloidal mill. Thereafter the resulting powder is transferred to 0.5 l of water containing 2% of lecithin (egg yolk lecithin purchased from Engelhardt & Co AB, of Sweden) at room temperature and stirred at 20000 rpm with a thurrax. After 10 minutes of stirring the phytosterol microparticles are separated from the water solution by means of filtration and dried under vacuum. Yield: 96.3 g of phytosterol microparticles with an average size of 15 μm.

Example 3

70 g of phytosterols, 26 g of stearic acid and 4 g of monoglyceryl stearate are mixed and melted by heating to yield a homogenous solution at an estimated solidification point of approximately 94° C. The solution is cooled and transferred to and milled in a Colloidal mill. Thereafter the resulting powder is transferred to 0.5 l of water containing 0.5% of di-sodium carbonate at room temperature and stirred at 20000 rpm with a thurrax. After 10 minutes of stirring the phytosterol microparticles are separated from the water solution by means of filtration and dried under vacuum. Yield: 98 g of phytosterol microparticles with an average size of 15 μm.

Example 4

70 g of phytosterols, 28 g of stearic acid and 2 g of monoglyceryl laurate are mixed and melted by heating to yield a homogenous solution at an estimated solidification point of approximately 99° C. The solution is cooled and transferred to and milled in a Colloidal mill. Thereafter the resulting powder is transferred to 0.5 l of water containing 0.5% of pectin at room temperature and stirred at 20000 rpm with a thurrax. After 10 minutes of stirring the phytosterol microparticles are separated from the water solution by means of filtration and dried under vacuum. Yield: 99.6 g of phytosterol microparticles with an average size of 15 μm.

Example 5

75 g of phytosterols, 23.5 g of stearic acid, 0.5 g sodium stearate and 1 g of monoglyceryl myristate are mixed and melted by heating to yield a homogenous solution at an estimated solidification point of approximately 105° C. The solution is cooled and transferred to and milled in a mill. Thereafter the resulting powder is transferred to 0.5 l of aqueous solution of 0.1% of pectin at room temperature and stirred at 100 rpm with a household blender of paddle type. After 30 minutes of stirring the phytosterol microparticles are separated from the water solution by means of filtration and dried under vacuum. Yield: 98.3 g of phytosterol microparticles with an average size of 15 μm.

Example 6

70 g of phytosterols, 27 g of palmitic acid 3 g of monoglyceryl myristate are mixed and melted by heating to yield a homogenous solution at an estimated solidification point of approximately 90° C. The solution is cooled and transferred to and milled in a mill. Thereafter the resulting powder is transferred to 0.3 l of aqueous solution of 0.1% of pectin at room temperature and stirred at 2000 rpm with a thurrax. After 30 minutes of stirring the phytosterol microparticles are separated from the water solution by means of filtration and dried at 30° C. Yield: 96.3 g of phytosterol microparticles with an average size of 25 μm.

Example 7

70 g of phytosterols, 26 g of stearic acid and 4 g of monoglyceryl myristate are mixed and melted by heating to yield a homogenous solution at an estimated solidification point of approximately 95° C. The solution is cooled and transferred to and milled in a Colloidal mill. Thereafter the resulting powder is transferred to 0.5 l of water at room temperature and stirred at 20000 rpm with a thurrax. After 10 minutes of stirring the phytosterol microparticles are separated from the water solution by means of filtration and dried under vacuum.

50 g of the resulting product powder is blended with 30 g of xylitol, 10 g of pregelatinized maize starch, 4 g of ascorbic acid, 0.5 g of aspartame and 0.8 g of menthol. The blend is directly compressed into chewable tablets of total weight 1.4 g containing 500 mg of phytosterols with excellent results with respect to friability, stability and sensory performance.

Example 8

70 g of phytosterols, 26 g of stearic acid and 4 g of monoglyceryl myristate are mixed and melted by heating to yield a homogenous solution at an estimated solidification point of approximately 95° C. The solution is cooled and transferred to and milled in a Colloidal mill. Thereafter the resulting powder is transferred to 0.5 l of water containing 2% of lecithin at room temperature and stirred at 20000 rpm with a thurrax. After 10 minutes of stirring the phytosterol microparticles are separated from the water solution by means of filtration and dried under vacuum. The product powder is granulated from an average particle size of 15 μm to 150 μm.

50 g of the resulting granulated product powder is blended with 5 g of micro crystalline cellulose, 10 g of pregelatinized maize starch, 4 g of sodium croscarmellose and 2 g of magnesium stearate. The blend is directly compressed into a tablet of total weight 1 g containing 700 mg of phytosterols with excellent results with respect to friability, stability and sensory performance.

Clinical Study

A preliminary clinical study made using tablets obtained in accordance with the principles described in the invention has confirmed that highly physiologically active phytosterol microparticles can be obtained and maintained in a final tablet form. Two healthy individuals daily consumed 3 chewable tablets containing 500 mg of phytosterols in the form of amorphous highly active microparticles for the duration of one month (total daily dosage: 1.5 g phytosterol). The chewable tablets were consumed in conjunction with meals.

Prior to commencing consumption, two blood samples were drawn two weeks apart to establish baseline values for triglyceride, HDL-cholesterol and LDL-cholesterol serum concentrations and also concentrations of apolipoprotein Al and apolipoprotein B. Serum concentrations for the mentioned components were then determined once per week for the duration of 30 days. After 30 days two blood samples were drawn two weeks apart in order to establish post consumption values for the blood components.

The results yielded a statistically significant decrease in LDL-cholesterol concentration by 21.5% (individually 29 and 14%) and a total cholesterol decrease by 16.4% (individually 19.1 and 13.6%), no statistically significant effects were measured for HDL-cholesterol or triglyceride concentrations. The results are considerably better than typically measured in clinical trials on phytosterol enriched foods. Notably, a cholesterol lowering could be detected within the first week of initiation of consumption and within the second week measurements obtained remained stable at a lower level than in the baseline measurements.

After halting consumption the cholesterol concentrations resurged to comparable levels as in the baseline measurements within a period of two weeks. Interestingly, values for apolipoprotein B were seen to diminish, yielding a statistically significant 8% decrease at the end of the 4 week consumption period. Apolipoprotein B is nowadays considered to be a more accurate marker of risk for contracting cardio-vascular disease than total cholesterol or LDL-cholesterol. Apolipoprotein B is found in one copy for each particle of LDL, VLDL or IDL (Low Density, Very Low Density and Intermediate Density Lipoprotein) particles, whereas apolipoprotein A1 is associated with HDL-particles. Thus, the number of circulating particles, rather than their content of cholesterol can be used as a marker for However, in general it is seldom measured due to practical reasons and consequently total cholesterol or LDL-cholesterol concentrations remain the most commonly applied markers for risk of developing cardio-vascular disease.

REFERENCES

1. Wood, D.; de Backer, G.; Faergeman, O.; Graham, I.; Mancia, G.; Pyorala, K. et al. *European Heart Journal*, 1998, 19, 1434.
2. Grundy, S. M.; Cleeman, J. I.; Daniels, S. R.; Donato, K. A.; Eckel, R. H.; Franklin, B. A.; Gordon, D. J.; Krauss, R. M.; Savage, P. J.; Smith, S. C. Jr.; Spertus, J. A.; Costa, F. *Circulation*, 2005, 112, 2735.
3. Law, M. R.; Wald, N. J.; Thompson, S. G. *Br. Med. J.* 1994, 308, 367.
4. McQueen M J; Hawken S; Wang X; Ounpuu, S; Sniderman, A; Probstfield, J; Steyn, K; Sanderson, J. E.; Hasani, M.; Volkova, E.; Kazami, K.; Yusuf, S. *Lancet* 2008, 372 (9634), 224-33
5. Stryer, L. *Biochemistry* $4^{th}$ ed. W. H. Freeman and C:o: New York 1995 p. 691-710.
6. Moss, G. P. *The nomenclature of steroids. Recommendations* IUPAC—The International Union of Pure and Applied Chemistry *Eur. J. Biochem.* 1989, 186, 429.
7. *Methods in Plant Biochemistry vol.* 7 Goad, J. L.; Charlewood, B. V.; Banthorpe, D. V. eds. London: Academic Press 1991 p. 369-434.
8. Akihisa, T.; Kokke, W. C. M. C.; Tamura, T. *Physiology and Biochemistry of sterols* Patterson, G. W.; Nes W. D. eds. American Oil Chemists Society 1991 p. 118-157.
9. Moreau, R. A.; Whitaker, B. D.; Hicks, K. B. *Progress Lipid Res.* 2002, 41, 457.
10. Piironen, V.; Lindsay, D. G.; Miettinen, T. A.; Toivo, J.; Lampi, A.-L. *J. Sci. Food Agric.* 2000, 80, 939.
11. Peterson, D. W. *Proc. Soc. Exp. Med. Biol.* 1951, 78, 143.
12. Pollak. O. J.; Kritchevsky, D. A. *Monographies in Atherosclerosis: Sitosterol* Karger: Basel 1981.
13. Katan, M.; Grundy, S. M.; Jones, P.; Law, M.; Miettinen, T.; Paoletti, R. *Mayo Clin. Proc.* 2003, 78, 965.
14. Mattson, F. M. Grundy, S. M.; Crouse, J. R. *Am. J. Clin. Nutr.* 1982, 35, 697.

15. McPherson, T. B.; Ostlund, R. E.; Goldberg, A. C.; Bateman, J. H.; Schimmoeller, L; Spilburg, C. A. *J. Pharm. Pharmacol.* 2005, 57, 889.

The invention claimed is:

1. Porous dry microparticles containing phytosterol, prepared by:
   (1) preparing a homogeneous melt of a composition comprising:
      (i) 60-80 wt % of a phytosterol component,
      (ii) 20-40 wt % of two partially water soluble components, the two components selected from:
         (a) at least one C10 to C26 fatty acid, and
         (b) at least one monoglyceride of a C10 to C26 fatty acid,
      said two components present in a weight ratio of (a) fatty acid to (b) monoglyceride of fatty acid in a range of greater than 6:1 to 30:1;
   (2) allowing the melt to solidify to an amorphous solid material;
   (3) processing the amorphous solid material into a fine powder;
   (4) stirring the powder in an aqueous phase to allow a portion of the partially water soluble components to dissolve, producing the porous microparticles; and
   (5) separating the porous microparticles from the aqueous phase, and
   (6) drying the porous microparticles.

2. The porous dry microparticles according to claim 1, wherein:
   (a) the fatty acid is stearic acid, palmitic acid or a combination thereof; and
   (b) the monoglyceride of a fatty acid is mono-glyceryl myristate, mono-glyceryl stearate, mono-glyceryl laurate or a combination thereof.

3. The porous dry microparticles according to claim 1, wherein the weight ratio of fatty acid to monoglyceride of a fatty acid is in a range of 6.5:1 to 24:1.

4. The porous dry microparticles according to claim 1, wherein:
   the fatty acid is stearic acid; and
   the monoglyceride of a fatty acid is mono-glyceryl myristate.

5. The porous dry microparticles according to claim 1, wherein the microparticles have a surface area of 100 m²/g to 500 m²/g of phytosterol.

6. The porous dry microparticles according to claim 1, wherein the microparticles have a particle size of 10 to 100 µm.

7. The porous dry microparticles according to claim 1, wherein the microparticles have a particle size of 15 to 40 µm.

8. The porous dry microparticles according to claim 1, wherein the composition further comprises: (iii) a diglyceride of a C10 to C26 fatty acid or a metal salt of a C10 to C26 fatty acid.

9. A food product enriched in phytosterol, prepared with the porous dry microparticles according to claim 1.

10. A tablet or pill, comprising the porous dry microparticles according to claim 1 and a pharmaceutically acceptable carrier.

11. The tablet or pill according to claim 10, comprising about 0.5 g of phytosterol.

12. A pharmaceutical formulation for lowering blood cholesterol in a mammal, prepared with the porous dry microparticles according to claim 1 and a pharmaceutically acceptable carrier.

13. Granulated particles, comprising the porous dry microparticles according to claim 1, the granulated particles having a size of 100-1000 µm.

14. A food product enriched in phytosterol, prepared with the granulate according to claim 13.

15. A method of preparing porous dry microparticles containing phytosterol, comprising:
   preparing a homogeneous melt of a composition comprising:
      (i) 60-80 wt % of a phytosterol component,
      (ii) 20-40 wt % of two partially water soluble components, the two components selected from:
         (a) at least one C10 to C26 fatty acid, and
         (b) at least one monoglyceride of a C10 to C26 fatty acid,
      said two components present in a weight ratio of (a) fatty acid to (b) monoglyceride of fatty acid in a range of greater than 6:1 to about 30:1, and
      (iii) optionally, a diglyceride of a C10 to C26 fatty acid, a metal salt of a C10 to C26 fatty acid and/or a surfactant;
   allowing the melt to solidify to an amorphous solid material;
   processing the amorphous solid material into a fine powder;
   stirring the powder in an aqueous phase to allow a portion of the partially water soluble components to dissolve, producing the porous microparticles;
   separating the porous microparticles from the aqueous phase; and
   drying the porous microparticles.

16. A method of reducing a blood level of cholesterol of a mammal, comprising administering to said mammal a pharmaceutical formulation or a food product prepared with the porous dry microparticles according to claim 1.

* * * * *